United States Patent
Peuker

(10) Patent No.: US 8,329,656 B2
(45) Date of Patent: Dec. 11, 2012

(54) USE OF A PDE5 INHIBITOR FOR TREATING AND PREVENTING HYPOPIGMENTARY DISORDERS

(75) Inventor: Heidmarie Peuker, Penzberg (DE)

(73) Assignee: Switch Biotech AG, Neuried (DE)

( * ) Notice: Subject to any disclaimer, the term of this patent is extended or adjusted under 35 U.S.C. 154(b) by 113 days.

(21) Appl. No.: 13/032,318

(22) Filed: Feb. 22, 2011

(65) Prior Publication Data

US 2011/0142956 A1     Jun. 16, 2011

Related U.S. Application Data

(62) Division of application No. 11/660,351, filed as application No. PCT/EP2005/007747 on Jul. 15, 2005.

(60) Provisional application No. 60/603,069, filed on Aug. 19, 2004.

(30) Foreign Application Priority Data

Aug. 19, 2004 (EP) .................................... 04019695

(51) Int. Cl.
  *A61P 17/00*    (2006.01)
  *A61K 31/497*   (2006.01)
(52) U.S. Cl. .................. 514/18.6; 514/252.16; 514/250; 514/262.1; 514/343
(58) Field of Classification Search ................ 514/18.6, 514/252.16, 250, 262.1, 262, 343
  See application file for complete search history.

(56) References Cited

U.S. PATENT DOCUMENTS

| 6,338,862 B1 | 1/2002 | Niazi |
| 2002/0182162 A1 | 12/2002 | Shahinpoor et al. |
| 2003/0096827 A1 | 5/2003 | Yu et al. |

FOREIGN PATENT DOCUMENTS

| DE | 198 34 505 | 2/2003 |
| EP | 1 092 719 | 4/2001 |
| WO | WO 03/063875 | 8/2003 |
| WO | WO 03/074082 | 9/2003 |
| WO | WO 2004/044234 | 5/2004 |
| WO | WO 2004/067006 | 8/2004 |
| WO | WO 2004/096222 | 11/2004 |

OTHER PUBLICATIONS

DeYoung, .L. et al., "Effect of PDE5 inhibition combined with free oxygen radical scavenger therapy on erectile function in a diabetic animal model", International Journal of Impotence Research, vol. 15, No. 6, 2003, United Kingdom, pp. 347-354.
Christ, B. et al, "Investigation on interaction between tacrolimus and sildenafil in kidney-transplanted patients with erectile dysfunction", International Journal of Clinical Pharmacology and Therapeutics, vol. 42, No. 3, Mar. 2004, pp. 149-156.
Khan, K.M. et al., "Synthesis of methyl ether analogues of sildenafil (Viagra ®) possessing tyrosinase inhibitory potential", Chemistry and Biodiversity, vol. 2, No. 4, 2005, Germany, pp. 470-476.
International Search Report for International Application No. PCT/EP2005/007747 dated Aug. 22, 2005.
Office Action for Japanese Patent Application No. JP2007-526325 dated Apr. 26, 2011.

*Primary Examiner* — Savitha Rao
(74) *Attorney, Agent, or Firm* — Pearl Cohen Zedek Latzer, LLP

(57) ABSTRACT

The invention relates to the use of PDE5 inhibitors for treating and/or preventing hypopigmentary disorders.

4 Claims, 1 Drawing Sheet

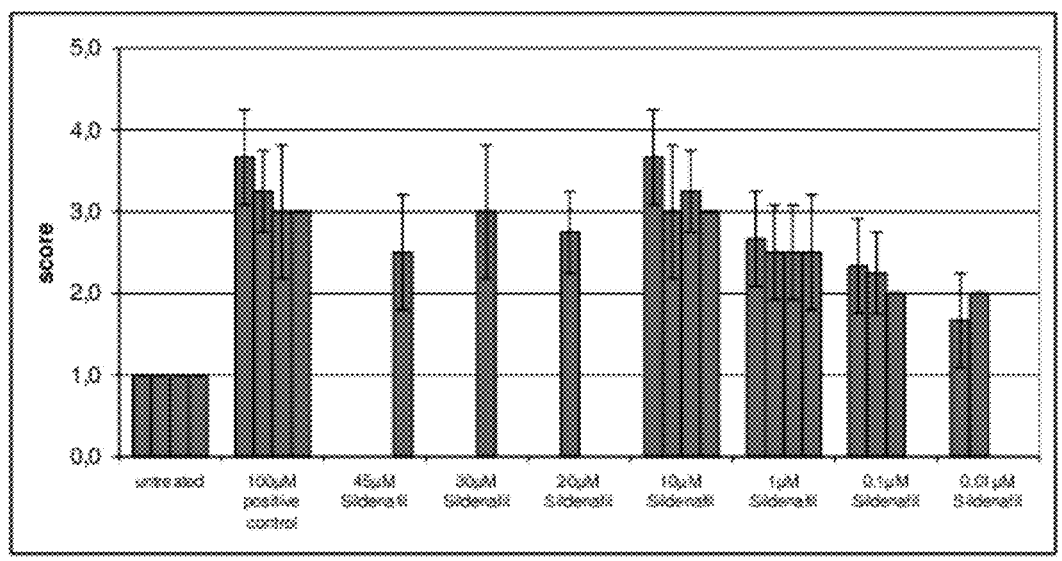

USE OF A PDE5 INHIBITOR FOR TREATING AND PREVENTING HYPOPIGMENTARY DISORDERS

CROSS REFERENCE TO PRIOR APPLICATION

The present application is a divisional of U.S. patent application Ser. No. 11/660,351, filed Jul. 5, 2007, which is a national phase application of International Patent Application No. PCT/EP2005/007747, filed Jul. 15, 2005, which in turn claims priority from European Patent Application No. 04019695.8 and U.S. Patent Application No. 60/603,069, both filed Aug. 19, 2004, all of which are incorporated by reference in their entireties.

FIELD OF THE INVENTION

The invention relates to the use of PDE5 inhibitor, or of an isomer thereof, or of a pharmaceutically acceptable salt thereof for treating and/or preventing hypopigmentary disorders. In particular, the invention relates to the use of Tadalafil and/or Sildenafil, its isomers and pharmaceutically acceptable salts for treating and/or preventing hypopigmentary disorders. The invention also relates to methods of treatment and or prevention of hypopigmentary disorders by administering PDE5 inhibitors.

BACKGROUND OF THE INVENTION

In the skin or hair, melanocytes are the sole source of the pigment melanin. Melanin is synthesized within the melanocytes and later transferred to the surrounding keratinocytes. The colour of the skin is determined to a large extent by the amount and type of melanin within the epidermis. In general dysfunction of the melanocytes or the loss of the melanocytes itself leads to loss of pigmentation. The mechanisms for the destruction of melanocytes are likely to be multiple and complex, possibly a composite of several normal processes influencing melanocyte function, proliferation and/or survival. Also the pathomechanism of hyperpigmentary disorders is largely unclear.

Vitiligo, for example is a pigmentation disorder afflicting up to 2% of the worldwide population. It is a specific type of leukoderma manifested characteristically by depigmentation of the epidermis, best described as an acquired, progressive disorder that selectively destroys some or all melanocytes. The vitiligo disease is characterized by milky white macules on the skin, either due to missing melanin pigment or to complete absence of melanocytes in the dermo-epidermal junction of vitiligo areas. Vitiligo tends to be progressive throughout the life of affected individuals. Other disorders of hypopigmentation that are caused by a defect in melanin production or transfer include the Chediak-Higashi syndrome, Hermansky-Pudlak syndrome, the Waardenburg syndromes I-IV, the Angelman and Prader-Willi syndrome. Albinism instead is characterized by genetic defects that impede the synthesis of melanin. Piebaldism is characterized by the absence of melanin at birth due to a deficiency of melanocytes. During embryogenesis melanocytes fail to complete their migration from the neural crest to the epidermis. In vitiligo some melanocytes can be found in epidermis of early lesions that are only partially depigmented. In late lesions that were totally depigmented, there is complete absence of melanocytes. Also, there is a lack of knowledge about the pathophysiology and mechanisms underlying most pigmentary disorders.

At the moment there are still several hypotheses to explain the possible causes of vitiligo:
1) Autoimmune disease: Specific autoantibodies to melanocyte cell surface antigens are present in the circulation of most patients with vitiligo. These antibodies are unusual in persons with nonpigmentary skin diseases. Vitiligo antibodies are shown to have the functional capacity to kill pigment cells in vitro and can do so by two different mechanisms: complement-dependent cytotoxicity and antibody-dependent cellular cytotoxicity.
2) Self-destruction of melanocytes as a consequence of aberrant melanin biosynthesis: The autocytotoxic hypothesis is based on the observation that phenol and some of its derivatives are capable of killing pigment cells. Tyrosine, the substrate of the tyrosinase is itself a phenol derivative, is oxidized into melanin via a complex series of oxidative reactions. Some intermediates are capable of forming radicals. It is thought that melanin synthesis is confined within the melanosome to prevent these melanin precursors from diffusing into the cell where they might disrupt essential metabolic pathways.
3) Overproduction of neurotransmitters leading to death of melanocytes: Melanocytes are neural crest derived cells. A dysfunction of nervous function might be involved in the pathogenesis of vitiligo as shown by an altered balance of neuropeptides in vitiliginous skin. Neuropeptides are able to induce melanocyte dendricity and participate in the regulation of cell substrate adhesion, cell motility and shape. Neuropeptides may also regulate melanin synthesis or affect melanosomal transfer to surrounding keratinocytes.
4) More recently, also viral infections as well as oxidative stress and hormonal causes are discussed to be involved in the disease formation.
5) Although the pathogenesis of vitiligo is still not known, there is a genetic predisposition, demonstrated by the fact, that 40% of vitiligo patients have a positive family history for this disease.
6) A combination of some or all of above theories Currently, no satisfying treatments exist for pigmentary disorders. For example, at present, there is no specific therapy for Vitiligo available without side effects and no innovative therapeutic programs are under development. No single therapy predictably produces good results in all patients and the responses are highly variable: systemic photochemotherapy (PUVA) gives satisfactory results only in some early disease states, however, treatment is time-consuming and has a high risk of developing cancer after prolonged treatment. Other therapies comprise systemic steroids, e.g. prednisone, hydrocortisone or triamcinolone, which however are also not suitable for prolonged treatment. In some cases, transplantation of skin has given positive results. In extreme cases, where the depigmented area has become very large, total chemical depigmentation of the skin is performed to achieve a homogeneous coloring of the skin.

Similarly, no specific and satisfactory treatment exists for Pityriasis alba, a common hypopigmented dermatitis that occurs primarily in school-aged children. Usually this disorder is left untreated as treatments with corticosteroids or retinoic acid or PUVA treatment are not very efficient.

Some pigmentary disorders, like vitiligo, have only skin manifestations limited to the pigmentation alterations. However, these disorders nevertheless pose severe psychological problems to the patients, as the sharp borders of depigmented areas are readily apparent to other persons, especially when occurring in the face. Vitiligo can be disfiguring and stigmatising, thereby causing significant psychological problems due to reduced social acceptance. Also, vitiligo usually persists for the whole life.

There is therefore a need for a specific treatment of hypopigmentary disorders, preferably vitiligo.

BRIEF DESCRIPTION OF THE DRAWINGS

Further aspects of the present invention will become evident by the figures and the following examples which are given to merely illustrate the invention, not to limit the same.

FIG. 1 shows the influence of Sildenafil on dendrite formation in melanocytes in a melanocyte dendrite outgrowth assay.

DETAILED DESCRIPTION OF THE INVENTION

Surprisingly it was found, that PDE5 inhibitors are suitable for the treatment and prevention of hypopigmentary disorders, especially vitiligo. Especially preferred are the PDE5 inhibitors Sildenafil, Tadalafil and Vardenafil, in particular Tadalafil and Sildenafil.

Phosphodiesterase 5 or PDE5 is one member of a superfamily of cyclic nucleotide hydrolysing enzymes that specifically cleaves cyclic guanosine monophosphate (cGMP) which is a second messenger. PDE5 inhibitors have originally been proposed to be useful in the treatment of hypertension and angina, however, the main focus is now their use in the treatment of erectile dysfunction. Other suggested activities of PDE5 inhibitors are reversal of gastric emptying, lowering blood pressure and pulmonary hypertension (see Rotella D. P., 2001, Drugs of the Future, 26: 153-162). It has never been proposed that the compounds of the invention are useful in the treatment and/or prevention of hypopigmentary disorders.

A range of PDE5 inhibitors with proven or suggested potential for use as medicine are known up to know. Such PDE5 inhibitors, which can be used according to the invention and which are included by reference are:

Dihydrotriazolohydropurinone derivatives which are disclosed in WO 01/07441;
purinone derivatives which are described in WO 94/00453;
Pyrazolo[3,4-d]pyrimidinine-4-one derivatives which are described in EP 0636626; WO 96/28429; WO 96/28448; WO 94/28902; U.S. Pat. No. 5,294,612 and EP 0995751;
1,6-Dihydro-7H-pyrazolo-[3,4-d]pyrimidin-4-one derivatives which are described in EP 0201188; WO 88/00192; EP 0995750; EP 1057829; EP 1092720; WO 01/127101; WO 01/27112; WO 01/27113 and WO 00/27848;
Imidazotriazinone derivatives which are described in WO 99/24433, WO 99/67244; and EP 1092719;
Imidazoquinazolinone derivatives which are described in WO 99/64004;
Pyrazolopyridopyrimidine derivatives which are described in Krupinski et al., 2001, Bioorg. Med. Chem. Lett., 11: 2461-2464
Pyrrolopyrimidinone derivatives which are disclosed in WO 01/60825;
Quinazolinone and Pyridopyrimidone derivatives which are disclosed in WO 93/12095 and WO 94/05661 and JP 8104679; JP 07330777 and JP 07267961;
Fused pyrimidine derivatives which are disclosed in Lee et al., 1995, J. Med. Chem., 38: 3547-3557, WO 98/06722, WO 02/26745; DE 19752952; WO 99/55708; DE 19943815; DE 19944604; Jonas et al., 2002, Chem. Abstr. 136: 85819; WO 99/43674; WO 00/59912; WO 98/17668; WO 02/18389; U.S. Pat. No. 5,436,233; EP 728759; U.S. Pat. No. 5,525,604; WO 93/07124; WO 96/26940; WO 95/06648; WO 98/08848; WO 99/43679; WO 99/43674; DE 19942474; WO 01/12608; WO 00/15222 and WO 02/20489;
Pyrimidine derivatives which are described in WO 01/19802; WO 01/83460; WO 98/23597; EP 0640599, WO 96/05176, WO 98/07430, WO 99/42452, WO 01/05770 and WO 00/56719;
Isoquinoline derivatives which are disclosed in WO 98/38168, WO 00/12503; EP 128462 and JP 12281654;
Hexahydropyrazino-pyrido-indole-1,4-dione derivatives which are disclosed in WO 95/19978, WO 97/03675, U.S. Pat. No. 6,143,746, WO 96/32003, WO 95/19978, WO 97/03985, WO 01/80860, WO 01/808686, WO 00/66114, WO 02/10166, WO 02/28858, WO 97/43287, U.S. Pat. Nos. 6,306,870, 6,043,252 and WO 01/87038;
Anthranilic acid diamide derivatives which are disclosed in WO 95/18097 and WO 99/54284,
Pyridocarbazolone derivatives which are described in WO 98/53819, WO 99/26946, WO 00/32195 and WO 99/28319;
Indole and Benzimidazole derivatives which are disclosed in WO 96/32379, WO 99/51574, WO 98/15530, WO 97/24334, WO 99/00373, WO 00/39099, WO 99/00373, WO 00/34277, JP 101824549, WO 97/03070, WO 99/00350, WO 00/39099, WO 00/39097, WO 99/0372 and WO 99/21831;
Pyrazoloquinoline and pyrazolopyridine derivatives which are disclosed in U.S. Pat. No. 5,488,055 and WO 96/28159;
Imidazopyridopyrazinones which are disclosed in WO 00/43392 and DE 19510965;
Quinazolinedione phtalimide derivatives which are disclosed in WO 01/44228 and WO 00/20412;
Cyclobutendione derivatives which are disclosed in WO 00/51973, WO 00/63170, WO 00/63160 and WO 94/29277;
Dual PDE1/5 inhibitors which are disclosed in WO 91/19717 and WO 97/19947
(see Haning et al., Progress in Medicinal Chemistry, 2003, 41: 249-306 for a review on PDE 5 inhibitors).

PDE5 inhibitors for the use according to the present invention include: the pyrazolo[4,3-d]pyrimidin-7-ones disclosed in EP-A-0463756, especially Sildenafil and salts and hydrates thereof; the pyrazolo[4,3-d]pyrimidin-7-ones disclosed in EP-A-0526004; the pyrazolo[4,3-d]pyrimidin-7-ones disclosed in published international patent application WO 93/06104; the isomeric pyrazolo[3,4-d]pyrimidin-4-ones disclosed in published international patent application WO 93/07149; the quinazolin-4-ones disclosed in published international patent application WO 93/12095; the pyrido[3,2-d]pyrimidin-4-ones disclosed in published international patent application WO 94/05661; the purin-6-ones disclosed in published international patent application WO 94/00453; the pyrazolo[4,3-d]pyrimidin-7-ones disclosed in published international patent application WO 98/49166; the pyrazolo[4,3-d]pyrimidin-7-ones disclosed in published international patent application WO 99/54333; the pyrazolo[4,3-d]pyrimidin-4-ones disclosed in EP-A-0995751; the pyrazolo[4,3-d]pyrimidin-7-ones disclosed in published international patent application WO 00/24745; the compounds disclosed in published international application WO95/19978; the compounds disclosed in published international application WO 99/24433 and the compounds disclosed in published international application WO 93/07124.

It is to be understood that the contents of the above published patent applications, and in particular the general formulae and exemplified compounds therein are incorporated herein in their entirety by reference thereto.

PDE5 inhibitors which may be used according to the invention include 3-ethyl[2-(4-morpholinylmethyl)benzylamino]-2,3-dihydro-1H-imidazo[4,5-g]quinazoline-2-thione; 1-(2-chlorobenzyl)-3-isobutyryl-2-propylindole carboxamide; 9-bromo-2-(3-hydroxypropoxy)-5-(3-pyridylmethyl)-4H-pyrido[3,2,1-jk]-carbazol-4-one; 4-(1,3-benzodioxol-5-ylmethylamino)-2-(1-imidazolyl)-6-methylthieno[2,3-d]pyrimidine; 6-(2-isopropyl-4,5,6,7-tetrahydropyrazolo[1,5-a]pyridine-3-yl)-5-methyl)-5-methyl-2,3,4,5-tetrahydropyridazin-3-one; 5-(4-methylbenzyl)-3-(1-methyl-4-phenylbutyl)-3,6-dihydro[1,2,3]triazolo[4,5-d]pyrimidin-7-one; 3-(1-methyl-4-phenylbutyl)-5-pyridin-4-ylmethyl-3,6-dihydro[1,2,3]triazolo[4,5-d]pyrimidin-7-one; 5-(4-bromobenzyl)-3-(1-methyl-4-phenylbutyl)-3,6-dihydro[1,2,3]-triazolo[4,5-d]pyrimidin-7-one; 5-benzyl-3-(1-methyl-4-phenylbutyl)-3,6-dihydro-[1,2,3]-triazolo[4,5d]pyrimidin-7-one; 5-(3,4-dimethoxybenzyl) (I-methyl phenylbutyl)-3,6-dihydro-[1,2,3]-triazolo-[4,5d]pyrimidin-7-one; 5-(3,4-dichlorobenzyl)-3-(1-methyl-4-phenylbutyl)-3,6-dihydro-[1,2,3]-triazolo[4,5d]pyrimidin-7-one; 5-biphenyl-4-ylmethyl-3-(1-methyl-4-phenylbutyl)-3,6-dihydro-[1,2,3]-triazolo[4,5d]pyrimidin-7-one; 5-(4-aminobenzyl)-3-(1-methyl-4-phenylbutyl)-3,6-dihydro-[1,2,3]-triazolo[4,5-d]pyrimidin-7-one; 5-(hydroxyphenylmethyl)-3-(1-methyl-4-phenylbutyl)-3,6-dihydro-[1,2,3]-triazolo-[4,5d]pyrimidin-7-one; 5-benzo[1,3]-dioxol-5-ylmethyl-3-[1-methyl-4-phenylbutyl]-3,6-dihydro[1,2,3]-triazolo[4,5-d]pyrimidin-7-one; N-4-[3-(1-methyl-4-phenylbutyl)-7-oxo-6,7-dihydro-3H-[1,2,3]-triazolo-[4,5-d]pyrimidin-5-ylmethyl]phenylacetamide; 5-benzoyl-3-(1-methyl-4-phenylbutyl)-3,6-dihydro-[1,2,3]triazolo[4,5-d]-pyrimidin-7-one; 3-(1-methyl-4-phenylbutyl)-5-[4-(morpholine-4-sulphinyl)benzyl]-3,6-dihydro[1,2,3]triazolo[4,5-d]pyrimidin-7-one; 3-(1-methyl-4-phenylbutyl)-5-[3-(morpholine-4-sulphonyl)benzyl]-3,6-dihydro[1,2,3]triazolo[4,5-d]pyrimidin-7-one; N-methyl-4-[3-(1-methyl-4-phenylbutyl)-7-oxo-6,7-dihydro-3H-[1,2,3]-triazolo-[4,5-d]pyrimidin-5-ylmethyl]-benzenesulphonamide; N-(2-dimethylaminoethyl)-4-[3-(1-methyl-4-phenylbutyl)-7-oxo-6,7-dihydro-3H-[1,2,3]triazolo[4,5-d]pyrimidin-5-ylmethyl]benzenesulphonamide; N-(2-hydroxyethyl)-4-[3-(1-methyl-4-phenylbutyl)-7-oxo-6,7-dihydro-3H-[1,2,3]triazolo[4,5-d]pyrimidin-5-ylmethyl]benzenesulphonamide; ethyl 1-[3-[3-(1-methyl-4-phenylbutyl)-7-oxo-6,7-dihydro-3H-[1,2,3]-triazolo-[4,5-d]pyrimidin-5-ylmethyl]benzenesulphonyl]piperidinecarboxylate; 3-(1-methyl-4-phenylbutyl)-5-[4-(4-methylpiperazin-1-sulphonyl)benzyl]-3,6-dihydro-[1,2,3]triazolo[4,5-d]pyrimidin-7-one; 5-benzo[1,3]dioxol-5-ylmethyl-3-[1-ethyl-heptyl]-3,6-dihydro-[1,2,3]-triazolo[4,5-d]pyrimidin-7-one; 3-[1-(1-hydroxyethyl)-4-phenylbutyl]-5-[4-(morpholine-4-sulphonyl)benzyl]-3,6-dihydro-[1,2,3]triazolo[4,5-d]pyrimidin-7-one; 5-[6-fluoro-1-(phenylmethyl)-1H-indazol-3-yl]-2-furanmethanol; 1-benzyl-6-fluoro-3-[5-(hydroxymethyl)furan-2-yl]-1H-indazole; 2-(1H-imidazol-1-yl)-6-methoxy-4-(2-methoxyethylamino)quinazoline; 1-[[3-(7,8-dihydro-8-oxo-1H-imidazo[4,5-g]quinazolin-6-yl)-4-propoxyphenyl]sulphonyl]-4-methylpiperazine; 4-(3-chloro-4-methoxybenzylamino)-1-(4-hydroxypiperidin-1-yl)phthalazine-6-carbonitrile; 1-[6-chloro-4-(3,4-methylendioxybenzylamino)quinazolin-2-yl]piperidin-4-carboxylic acid; (6R,12aR)-6-(1,3-benzodioxol-5-yl)-2-methyl-1 2,3,4,6,7,12,12a-octa-hydropyrazino[2',1':6,1]pyrido[3,4-b]indole-1,4-dione (Tadalafil); (6R,12aR)-2,3,6,7,12,12a-hexahydro-2-methyl-6-(3,4-methylenedioxyphenyl)-pyrazino[2',1':6,1]pyrido[3,4-b]indole-1,4-dione; 4-ethoxy-2-phenylcycloheptylimidazole; (6-bromo-3-methoxymethylimidazo[1,2-a]pyrazin-8-yl)methylamine; 8-[(phenylmethyl)thio]-4-(1-morpholinyl)-2-(1-piperazinyl)pyrimidino[4,5-d]pyrimidine; (+)-cis-5-methyl-2-[4-(trifluoromethyl)benzyl]-3,4,5,6a,7,8,9-octahydrocyclopent[4,5]imidazo[2,1-b]purin-4-one; cis-2-hexyl-5-methyl-3,4,5,6a,7,8,9,9a-octahydrocyclopent[4,5]imidazo[2,1-b]purin-4-one; 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (Sildenafil); 1-[[3(6,7-dihydro-1-methyl-7-oxo-3-propyl-1H-pyrazolo[4,3-d]pyrimidin-5-yl)-4-ethoxyphenyl]sulfonyl]-4-methylpiperazine; 2-(2-propoxyphenyl)purin-6(1H)-one; 2-(2-propoxyphenyl)-1,7-dihydro-5H-purin-6-one; methyl 2-(2-methylpyridin-4-ylmethyl)-1-oxo-8-(2-pyrimidinylmethoxy)-4-(3,4,5-trimethoxyphenyl)-1,2-dihydro-[2,7]naphthyridin-3-carboxylate; methyl 2-(4-aminophenyl)-1-oxo-7-(2-pyridinylmethoxy)-4-(3,4,5-trimethoxyphenyl)-1,2-dihydroisoquinoline-3-carboxylate; 2-[2-ethoxy-5-(4-ethylpiperazin-1-ylsulfonyl)phenyl]-5-methyl-7-propylimidazo[5,1-f][1,2,4]triazin-4(3H)-one (Vardenafil); 3,4-dihydro-6-[4-(3,4-dimethoxybenzoyl)-1-piperazinyl]-2-(1H)-quinolinone (vesnarinone); 1-cyclopentyl-3-methyl-6-(4-pyridyl)pyrazolo[3,4-d]pyrimidin-4(5H)-one; 1-cyclopentyl-6-(3-ethoxy-4-pyridin-8-azapurin-6-one; 3,6-dihydro-5-(o-propoxyphenyl)-7H-[1,2,3]triazolo[4,5-d]pyrimidin-7-one and 4-methyl-5-(4-pyridinyl)thiazole-2-carboxamide and the pharmacologically acceptable salts of these compounds.

Other PDE5 inhibitors useful in conjunction with the present invention include:
4-bromo-5-(pyridylmethylamino)-6-[3-(4-chlorophenyl)-propoxy]-3(2H)pyridazinone;
1-[4-[(1,3-benzodioxol-5-ylmethyl)amino]-6-chloro-2-quinozolinyl]-4-piperidine-carboxylic acid, monosodium salt;
(+)-cis-5,6a,7,9,9,9a-hexahydro-2-[4-(trifluoromethyl)-phenylmethyl-5-methyl-cyclopent-4,5]imidazo[2,1-b]purin-4(3H)one;
furazlocillin;
cis-2-hexyl-5-methyl-3,4,5,6a,7,8,9,9a-octahydrocyclopent[4,5]-imidazo[2,1-b]purin-4-one;
3-acetyl-1-(2-chlorobenzyl)-2-propylindole-6-carboxylate;
3-acetyl-1-(2-chlorobenzyl)-2-propylindole-6-carboxylate;
4-bromo-5-(3-pyridylmethylamino)-6-(3-(4-chlorophenyl)propoxy)-3-(2H)pyridazinone;
1-methyl-5(5-morpholinoacetyl-2-n-propoxyphenyl)-3-n-propyl-1,6-dihydro-7H-pyrazolo[4,3-d]pyrimidin-7-one;
1-[4-[(1,3-benzodioxol-5-ylmethyl)amino]-6-chloro-2-quinozolinyl]-4-piperidinecarboxylic acid, monosodium salt;
Pharmaprojects No. 4516 (Glaxo Wellcome); Pharmaprojects No. 5051 (Bayer);
Pharmaprojects No. 5064 (Kyowa Hakko; see WO 96/26940);
Pharmaprojects No. 5069 (Schering Plough); GF-196960 (Glaxo Wellcome); Bay-38-3045 & 38-9456 (Bayer);
(S)-2-(2-Hydroxymethyl-1-pyrrolidinyl)-4-(3-chloro-4-methoxybenzylamino)-5-[(2-pyrimidinylmethyl)carbamoyl]pyrimidine;
DA-8159 (Benzenesulfonamide, 3-(4,7-dihydro-1-methyl-7-oxo-3-propyl-1H-pyrazolo[4,3-d]pyrimidin-5-yl)-N-[2-(1-methyl-2-pyrrolidinyl)ethyl]-4-propoxy-);
EMD-221829;
UK 357903 (piperazine, 1-ethyl-4-[[5-[3-ethyl-4,7-dihydro-7-oxo-2-(2-pyridinylmethyl)-2H-pyrazolo[4,3-d]pyrimidin-5-yl]-6-(2-methoxyethoxy)-3-pyridinyl]sulfonyl]-);
UK 114542.

Preferred PDE5 inhibitors include:
BMS-341400 which has the following structure:

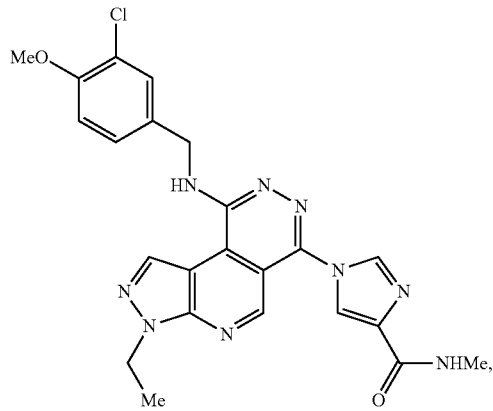

BMS-281384 which has the following structure:

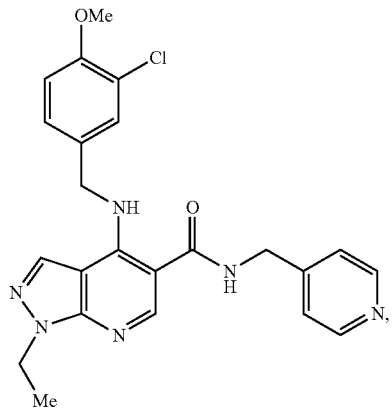

BMS-263504, LAS-34179, LAS-30902, LAS-34837, AWD-12-250,

OSI-461 (CAS RN No. 227619-96-7) which has the following structure:

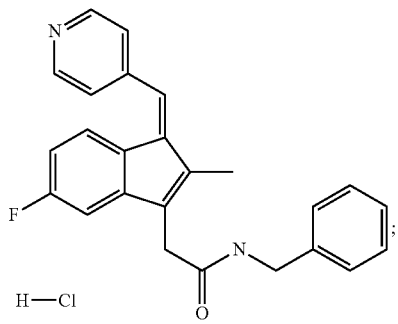

Exisulind which has the following structure:

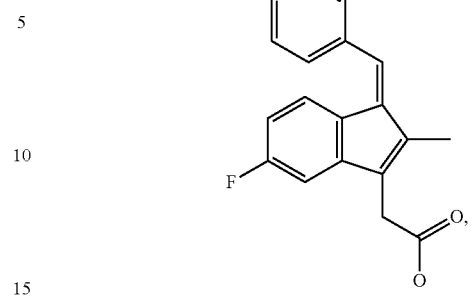

Sophoflavescenol which has the following structure:

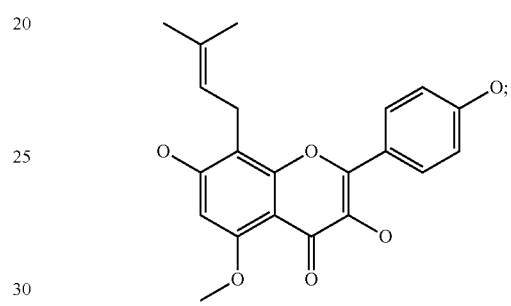

DA-8159 (Benzenesulfonamide, 3-(4,7-dihydro-1-methyl-7-oxo-3-propyl-1H-pyrazolo[4,3-d]pyrimidin-5-yl)-N-[2-(1-methyl-2-pyrrolidinyl)ethyl]-4-propoxy-);

E-8010 (6-Phthalazinecarbonitrile, 4-[[(3-chloro-4-methoxyphenyl)methyl]amino]-1-(4-hydroxy-1-piperidinyl)- and its monohydrochloride salt);

E4010 ([4-(3-chloro-4-methoxybenzyl)amino-1-(4-hydroxy)piperidino]-6-phthalazine carbonitrile monohydrochloride);

FR-181074; FR-226807 (Benzamide, N-[(3,4-dimethoxyphenyl)methyl]-2-[[(1R)-2-hydroxy-1-methylethyl]amino]-5-nitro-); FR-189318;

FR-229934, which has the following structure:

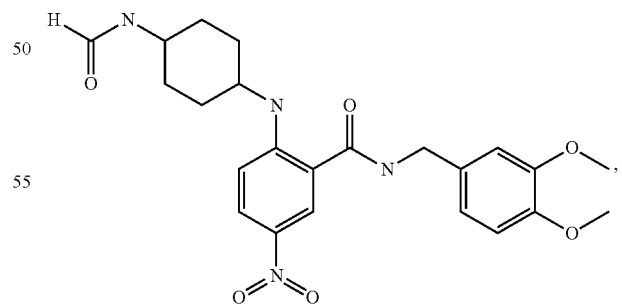

DMPPO, GF-248 (1-Methyl-5-(5-morpholinoacetyl-2-propoxyphenyl)-3-propyl-1,6-dihydro-7H-pyrazolo[4,3-d]pyrimidin-7-one), KF-31327 (3-Ethyl-8-[2-(4-hydroxymethylpiperidino) benzylamino]-2,3-dihydro-1H-imidazo[4,5-g]quinazoline-2-thione dihydrochloride); EMD-82639; EMR-62203; NCX-911 (Sildenafil nitrate);

NM-702 which has the following structure:

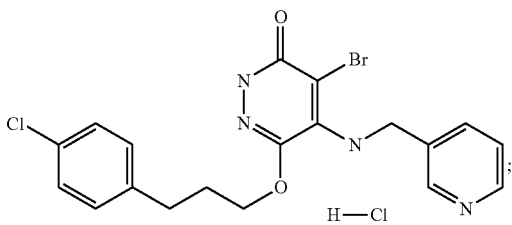

QAD-171A which has the following structure:

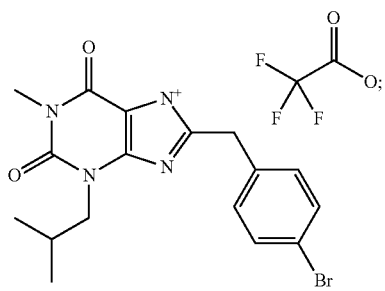

OPC-35564 which has the following structure:

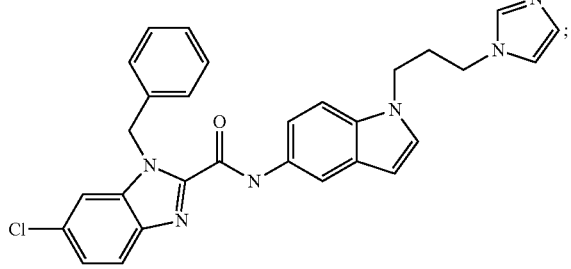

UK-114542; UK-357903; UK-369003;

UK-83405 which has the following structure:

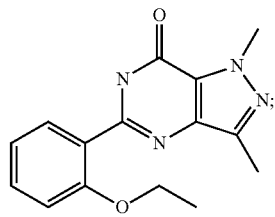

UK-114502; SR-265579 (4H-Pyrazolo[3,4-d]pyrimidin-4-one, 1-cyclopentyl-6-(3-ethoxy-4-pyridinyl)-3-ethyl-1,3a-dihydro-);

SCH-446132 which has the following structure:

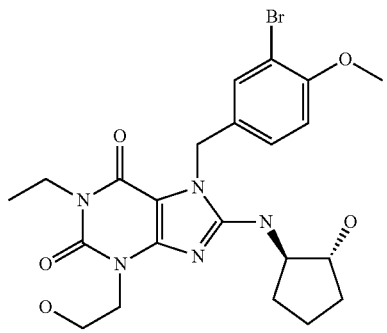

and which is disclosed in WO 00/224698;
Sch-51866 (Cyclopent[4,5]imidazo[2,1-b]purin-4(1H)-one, 5,6a,7,8,9,9a-hexahydro-5-methyl-2-[[4-(trifluoromethyl)phenyl]methyl]-, (6aR,9aS)-rel-) which has the following structure:

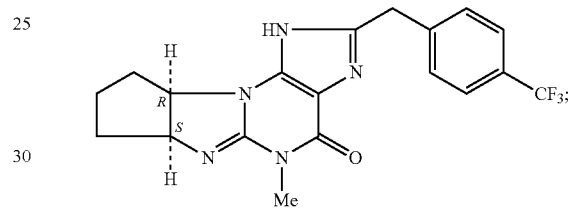

Sch-59498; SK-3530, SB-96231 (2-(2-Propoxyphenyl)-1,7-dihydro-6-purinone; SKF-96231); WIN-65579 (4H-Pyrazolo[3,4-d]pyrimidin-4-one, 1-cyclopentyl-6-(3-ethoxy-4-pyridinyl)-3-ethyl-1,7-dihydro-); Avanafil (5-Pyrimidinecarboxamide, 4-[[(3-chloro-4-methoxyphenyl)methyl]amino]-2-[(2S)-2-(hydroxymethyl)-1-pyrrolidinyl]-N-(2-pyrimidinylmethyl)-);
T-0156 which has the following structure:

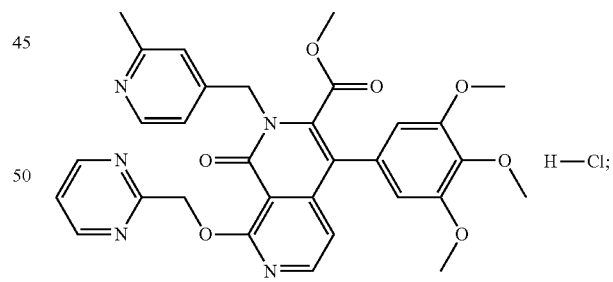

T-1032 (3-Isoquinolinecarboxylic acid, 2-(4-aminophenyl)-1,2-dihydro-1-oxo-7-(2-pyridinylmethoxy)-4-(3,4,5-trimethoxyphenyl)-, methyl ester, sulfate); YC-1 (2-Furanmethanol, 5-[1-(phenylmethyl)-1H-indazol-3-yl]-)
and salts and esters thereof, or, where the compound is already a salt, a different salt thereof.

Further preferred PDE5 inhibitors for the use according to the present invention include:
5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (Sildenafil) also known as 1-[[3-(4,7-dihydro-1-methyl-7-oxo-3-propyl-1H-pyrazolo[4,3-d]

pyrimidin-5-yl)-4-ethoxyphenyl]sulphonyl]-4-methylpiperazine ((see EP-A-0463756); see Example 1 of the present invention)

5-(2-ethoxy-5-morpholinoacetylphenyl)-1-methyl-3-n-propyl-1,6-dihydro-7H-pyrazolo[4,3-d]pyrimidin-7-one (see EP-A-0526004);

3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166);

3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333);

(+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine;

5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one;

5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one;

5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one;

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one;

(6R,12aR)-2,3,6,7,12,12a-hexahydro-2-methyl-6-(3,4-methylenedioxyphenyl)-pyrazino[2',1':6,1]pyrido[3,4-b]indole-1,4-dione (Tadalafil; IC-351; see Example 2 of the present application), i.e. the compound of examples 78 and 95 of published international application WO95/19978, as well as the compound of examples 1, 3, 7 and 8 of WO95/19978;

2-[2-ethoxy-5-(4-ethyl-piperazin-1-yl-1-sulphonyl)-phenyl]-5-methyl-7-propyl-3H-imidazo[5,1-f][1,2,4]triazin-4-one (Vardenafil) also known as 1-[[3-(3,4-dihydro-5-methyl-4-oxo-7-propylimidazo[5,1-f][1,2,4]triazin-2-yl)-4-ethoxyphenyl]sulphonyl]-4-ethylpiperazine, i.e. the compound of examples 20, 19, 337 and 336 of published international application WO99/24433; and the compound of example 11 of published international application WO93/07124 (EISAI); and compounds 3 and 14 from Rotella D P, J. Med. Chem., 2000, 43, 1257.

A particularly preferred PDE5 inhibitor of the present invention is Sildenafil, which has the following structure:

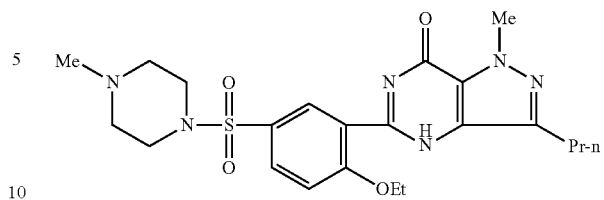

(I)

or a pharmaceutically acceptable salt thereof, in particular the citrate salt.

Alternative names for Sildenafil are 5-[2-Ethoxy-5-(4-methyl-1-piperazinylsulfonyl)phenyl]-1-methyl-3-n-propyl-1,6-dihydro-7H-pyrazolo[4,3-d]pyrimidin-7-one and 1-[[3-(4,7-dihydro-1-methyl-7-oxo-3-propyl-1H-pyrazolo[4,3-d]pyrimidin-5-yl)-4-ethoxyphenyl]sulfonyl]-4-methyl-piperazine. The synthesis of the compound is well known for a skilled person and for example described in described in EP 0 463 756B1. The CAS No. is 139755-83-2.

The preferred salt of Sildenafil useable according to the invention is Sildenafil citrate.

Another particularly preferred PDE5 inhibitor of the present invention is Tadalafil, which has the following structure:

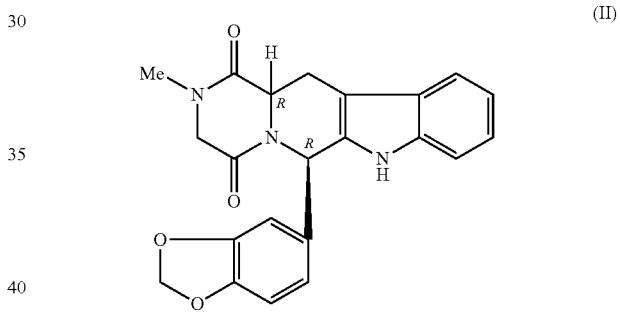

(II)

Alternative names for Tadalafil are Pyrazino[1',2':1,6]pyrido[3,4-b]indole-1,4-dione, 6-(1,3-benzodioxol-5-yl)-2,3,6,7,12,12a-hexahydro-2-methyl-, (6R,12aR)- and Pyrazino[1',2':1,6]pyrido[3,4-b]indole-1,4-dione, 6-(1,3-benzodioxol-5-yl)-2,3,6,7,12,12a-hexahydro-2-methyl-, (6R-trans)- and (6R,12aR)-2,3,6,7,12,12a-hexahydro-2-methyl-6-(3,4-methylenedioxyphenyl)pyrazino[1',2':1,6]pyrido[3,4-b]indole-1,4-dione and Cialis; GF 196960; IC 351 and ICOS 351. The synthesis of the compound is well known for a skilled person and for example described in described in WO 95/19978. The CAS Reg. No is 171596-29-5.

The suitability of any particular PDE5 inhibitor can be readily determined by evaluation of its potency and selectivity using literature methods followed by evaluation of its toxicity, absorption, metabolism, pharmacokinetics, etc in accordance with standard pharmaceutical practice.

Preferably, the PDE5 inhibitors have an $IC_{50}$ at less than 100 nanomolar, more preferably, at less than 50 nanomolar, more preferably still at less than 10 nanomolar.

$IC_{50}$ values for the PDE5 inhibitors may be determined using established literature methodology, for example as described in EP0463756 and EP0526004.

Preferably the PDE5 inhibitors used in the invention are selective for the PDE5 enzyme. Preferably they are selective over PDE3, more preferably over PDE3 and PDE4. Preferably, the PDE5 inhibitors of the invention have a selectivity ratio greater than 100, more preferably greater than 300, over PDE3 and more preferably over PDE3 and PDE4. The term "to have a selectivity ratio for enzyme z greater than x . . . over enzyme y", as used herein, is meant to designate that a compound/substance characterised by such term have an x-times greater preference for enzyme z than for enzyme y.

Selectivity ratios may readily be determined by the skilled person. $IC_{50}$ values for the PDE3 and PDE4 enzyme may be determined using established literature methodology, see S. A. Ballard et al, Journal of Urology, 1998, vol. 159, pages 2164-2171.

Surprisingly, the PDE5 inhibitors, such as Sildenafil and Tadalafil, can be used to treat hypopigmentary disorders, especially vitiligo. The present invention therefore relates to the use of a PDE5 inhibitor for the manufacture of a medicament for treating and/or preventing hypopigmentary disorders, especially vitiligo. Furthermore the present invention relates to a method of treating and/or preventing hypopigmentary disorders, especially vitiligo comprising administering to a mammal a PDE5 inhibitor.

Surprisingly it was found that compounds according to formula (I):

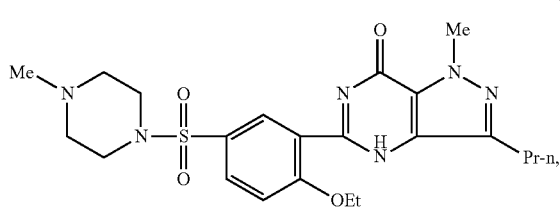

(I)

or isomers thereof or pharmaceutically acceptable salts thereof, are useful in the treatment and prevention of hypopigmentary disorders, especially vitiligo.

Moreover it was surprisingly found that a PDE5 inhibitor, especially Sildenafil, is especially suitable for the treatment and prevention of hypopigmentary diseases which have an inflammatory and/or autoimmune component and/or in which T cell activation and proliferation plays a role, especially preferred vitiligo. Such inflammatory and/or autoimmune component may form part of the hypopigmentary disease or may be in addition thereto.

The present invention therefore relates to the use of a compound according to formula

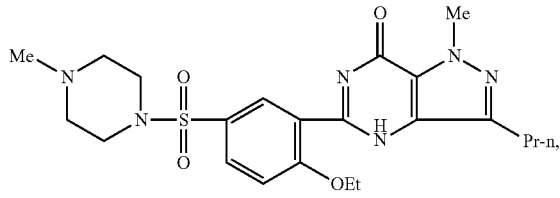

(I)

or an isomer thereof, or a pharmaceutically acceptable salt thereof, for the manufacture of a medicament for treating and/or preventing hypopigmentary disorders, especially vitiligo.

In a preferred embodiment, the compound is Sildenafil or a pharmaceutically acceptable salt thereof, in particular the citrate salt.

Surprisingly it was found that compounds according to formula (II)

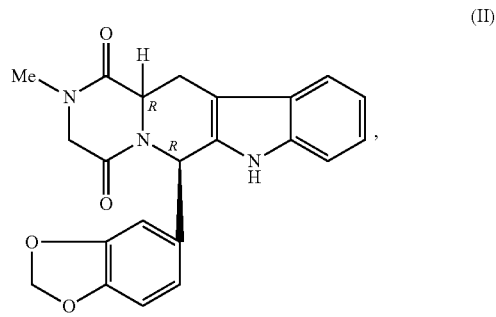

(II)

or isomers thereof or pharmaceutically acceptable salts thereof, are useful in the treatment and prevention of hypopigmentary disorders, especially vitiligo.

Moreover it was surprisingly found that a PDE5 inhibitor, especially Tadalafil is especially suitable for the treatment and prevention of hypopigmentary diseases which have an inflammatory and/or autoimmune component and/or in which T cell activation and proliferation plays a role, especially preferred vitiligo. Such inflammatory and/or autoimmune component may form part of the hypopigmentary disease or may be in addition thereto.

The present invention therefore relates to the use of a compound according to formula (II):

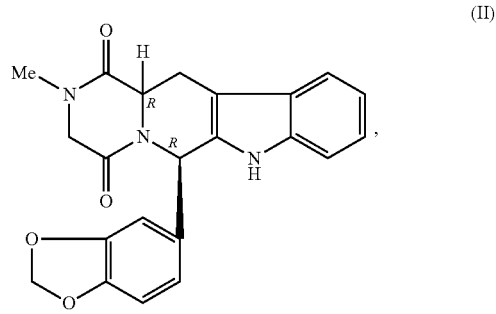

(II)

or an isomer thereof, or a pharmaceutically acceptable salt thereof, for the manufacture of a medicament for treating and/or preventing hypopigmentary disorders, especially vitiligo. In a preferred embodiment, the compound is Tadalafil or a pharmaceutically acceptable salt thereof.

The invention also relates to a method of treating and/or preventing hypopigmentary disorders, especially vitiligo, comprising administering to a mammal a compound according to formula (I):

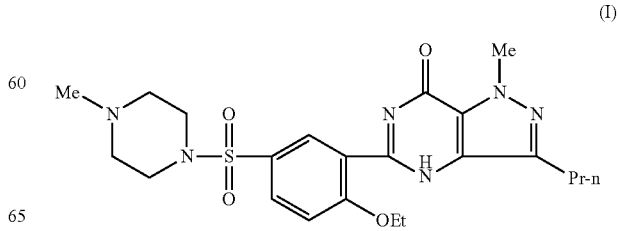

(I)

or an isomer thereof, or a pharmaceutically acceptable salt thereof, in particular the citrate salt.

In an even more preferred embodiment, the compound is selected from Sildenafil or a pharmaceutically acceptable salt thereof, in particular the citrate salt.

The invention also relates to a method of treating and/or preventing hypopigmentary disorders, especially vitiligo, comprising administering to a mammal a compound according to formula (II):

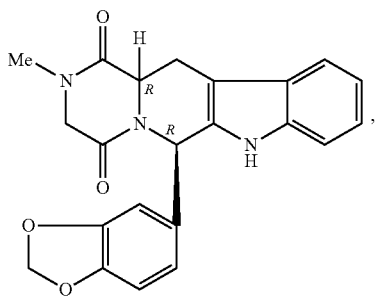
(II)

or an isomer thereof or a pharmaceutically acceptable salt thereof.

In an even more preferred embodiment, the compound is selected from Tadalafil or a pharmaceutically acceptable salt thereof.

In one embodiment, the hypopigmentary disorder has an inflammatory and/or an autoimmune component. Preferably the hypopigmentary disorder is selected from albinism, vitiligo, postinflammatory hypopigmentation, piebaldism, Pityariasis alba, Hypomelanoses, Leukodermas, hypopigmentation occurring e.g. after externally induced peels, e.g. chemical peels, e.g. with phenol, or laser or cryo-surgery of the skin, Chediak-Higashi syndrome, Hermansky-Pudlak syndrome, the Angelman and Prader-Willi syndrome, wherein, more preferably, the hypopigmentary disorder is a disorder in which T cell activation and proliferation plays a role, and which hypopigmentary disorder is more preferably selected from post-inflammatory hypopigmentation and vitiligo. In the most preferred embodiment, the hypopigmentary disorder is vitiligo.

Methods of production of the compounds according to the present invention are well known to someone skilled in the art, and are described e.g. in, the contents of the documents cited above which are hereby incorporated by reference.

Preferably, the medicament according to the present invention is prepared in a form suitable for topical use, preferably in form of an ointment, a gel, a plaster, an emulsion, a lotion, a foam, a cream, a cream of a mixed phase or amphiphilic emulsion system (oil/water-water/oil mixed phase), a liposome, a transfersome, a paste or a powder, or a solution or suspension.

In one embodiment, the compound is applied topically or systemically or via a combination of the two routes, preferably topically.

The objects of the present invention are also solved by a composition comprising a PDE5 inhibitor useable according to the invention and one or more further active ingredients suitable for the treatment and/or prevention of hypopigmentary disorders. Preferably, such composition is used as a pharmaceutical.

In a preferred embodiment the objects of the present invention are solved by a composition comprising a compound according to formula (I)

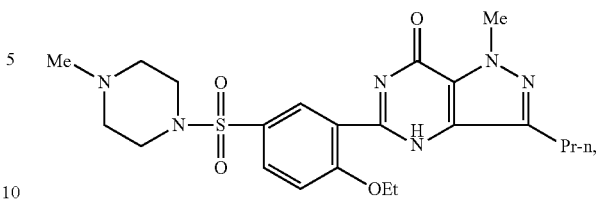
(I)

or an isomer thereof, or a pharmaceutically acceptable salt thereof, and one or more further active ingredients suitable for the treatment and/or prevention of hypopigmentary disorders.

In a preferred embodiment the objects of the present invention are also solved by a composition comprising a compound according to formula (II)

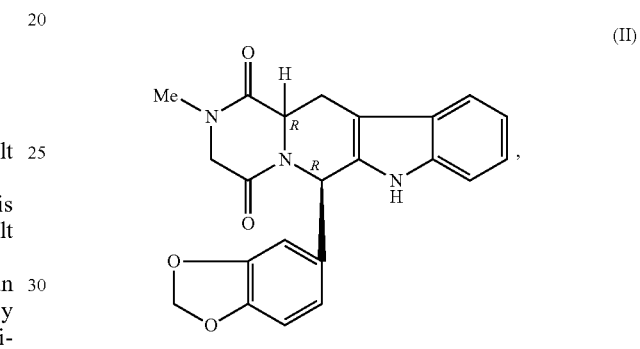
(II)

or an isomer thereof, or a pharmaceutically acceptable salt thereof, and one or more further active ingredients suitable for the treatment and/or prevention of hypopigmentary disorders. Preferably, such composition is used as a pharmaceutical.

In one embodiment, the further active ingredient is selected from the group consisting of cyclosporin A, cyclosporin G, cyclosporin B, cyclosporin C, cyclosporin D, dihydro-cyclosporin D, cyclosporin E, cyclosporin F, cyclosporin H, cyclosporin I, ASM-240, pimecrolimus, tacrolimus, 13-desmethyl-derivatives of tacrolimus (L-685487), L-683519 and/or 17-ethyl-derivatives of tacrolimus, preferably pimecrolimus, tacrolimus, or cyclosporin A, most preferably tacrolimus; steroids, in particular betamethasone, betamethasone-17-valerate, fluocinolone, triamcinolone, triamcinolone acetonide, clobetasol, clobetasol propionate, halobetasol, hydrocortisone, cortisone, desonide, prednisolone, paramethasone, methylprednisolone, dexamethasone, deflazacort; vitamin D analogues, in particular calcipotriol; pseudocatalase; levamisole, fluorouracil; alpha-MSH; clofazimine; thiambutosine BP; chloroquine; penicillamine; tar; minoxidil; inosiplex; mechlorethamine; cyclophosphamide; anapsos; antioxidants like *Gingko biloba,* canthaxanthine, beta-carotene, alpha-tocopherol, a combination of alpha-tocopherol ubiquinone seleno-methionine and methionine; pentoxifylline; vitamins and trace elements, in particular vitamin B12, folic acid, vitamin C, vitamin E, copper salts, human placental extract, khellin and phenylalanine.

Preferably, the composition according to the present invention is formulated for topical use, more preferably in form of an ointment, a gel, a plaster, an emulsion, a lotion, a foam, a cream, a cream of a mixed phase or amphiphilic emulsion system (oil/water-water/oil mixed phase), a liposome, a transfersome, a paste or a powder, or a solution or suspension.

The objects of the present invention are furthermore solved by the use of the composition according to the present invention for the manufacture of a medicament for the treatment and/or prevention of hypopigmentary disorders.

Hypopigmentary Disorders

Hypopigmentary disorders according to the present invention are non-malignant disorders of the skin in mammals, including humans which are characterized by a decrease in pigmentation of the skin compared to healthy individuals. Such decrease in pigmentation may occur locally, as e.g. in mild forms of vitiligo, or may affect the whole skin. Such decrease in pigmentation may result in total loss of pigmentation, as e.g. in affected skin areas of vitiligo patients, or may result in "lighter" but still pigmented skin as in Pityriasis alba. In some embodiments, the hypopigmentary disorders, according to the present invention, have an inflammatory and/or an autoimmune component. As used herein, the term "having an inflammatory component" is meant to designate any condition which is accompanied locally or temporally with syndromes characteristic of an inflammatory reaction, such as the induction of certain cytokines, in particular soluble IL-2R (sIL-2R), IL-6 and IL-8, and increased levels of inflammatory cells, in particular T-cells and macrophages, at sites of lesions or around lesions. Such inflammatory and/or an autoimmune component may form part of the hypopigmentary disorder or may be in addition thereto.

The term "accompanied temporally" may mean that the inflammatory component precedes the hypopigmentary disorder, is concomitant therewith or follows it.

The term "autoimmune component" in an organism is meant to designate any condition which is characterized by a reaction of the organism's own immune system against the organism itself or tissues or cells or other components thereof. An example of such a reaction is the production of auto-antibodies which are antibodies that are directed at some of an organism's own tissues or cells or other body components.

Examples of hypopigmentary disorders are, but not limited to, albinism, vitiligo, postinflammatory hypopigmentation, piebaldism, Pityriasis alba, Hypomelanoses, Leukodermas, hypopigmentation occurring e.g. after externally induced peels, e.g. chemical peels with phenol, or laser or cryo-surgery of the skin, Chediak-Higashi syndrome, Hermansky-Pudlak syndrome, the Angelman and Prader-Willi syndrome. An especially preferred hypopigmentary disorder of the present invention is vitiligo.

Examples of hypopigmentary disorders in which T cell activation and proliferation plays a role are postinflammatory hypopigmentation and vitiligo, preferably vitiligo.

Treatment according to the present invention relates to the complete or partial healing of the hypopigmentary disorder in mammals, including humans as well as to the stop or slowing-down of the progression of a hypopigmentary disorder. Also, the compounds of the present invention are suitable for the prevention of a hypopigmentary disorder in mammals, including humans.

Treatment of vitiligo according to the present invention relates to the complete or partial healing of the disorder vitiligo; i.e. complete or partial repigmentation of existing white macules on vitiligo patients, as well as to the stop or slowing-down of the extension of the white macule areas on vitiligo patients. Prevention of vitiligo according to the present invention relates to the prevention of occurrence of vitiligo phenotype in to date unaffected persons. Preferably, such unaffected persons are persons with higher risk of vitiligo; i.e. persons with a family history of vitiligo.

Pharmaceutical Compositions

Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in its free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvents such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the PDE5 inhibitors of the invention, its active metabolites or isomers and salts according to the invention and their application can be performed according to well-known pharmaceutical methods.

While the PDE5 inhibitors of the invention useable according to the invention for use in therapy may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the PDE5 inhibitors of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound useable according to the invention can be administered in a wide variety of oral and parenteral dosage forms. It will be obvious to those skilled in the art that the following dosage forms may comprise, as the active component, either a compounds useable according to the invention or a pharmaceutically acceptable salt of a compounds useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

In an especially preferred embodiment of the present invention the medicament is applied topically. This reduces possible side effects and limits the necessary treatment to those areas affected.

Preferably the medicament is prepared in form of an ointment, a gel, a plaster, an emulsion, a lotion, a foam, a cream, a cream of a mixed phase or amphiphilic emulsion system (oil/water-water/oil mixed phase), a liposome, a transfersome, a paste or a powder.

Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

For topical administration, the compounds of the present invention may be administered in a formulation containing 0.001% to 10% per weight of the compound, preferably between 0.01% to 10% per weight of the compound, even more preferred between 0.1% and 5% per weight of the compound.

Especially preferred are topical formulations of compounds of the invention, especially of Tadalafil and Sildenafil and salts and hydrates thereof, especially in an O/W emulsion (oil-in-water emulsion) or cream. The invention thus also relates to a composition suitable for topical use, comprising a compound of the invention, especially selected from Tadalafil and Sildenafil or a pharmaceutically acceptable salt thereof.

Compositions suitable for topical administration in the mouth include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

In another aspect the present invention relates to a composition comprising a PDE 5 inhibitor useable according to the invention or an isomer thereof, or a pharmaceutically acceptable salt thereof, and one or more further active ingredients which are known to be suitable for the treatment and/or prevention of hypopigmentary disorders, especially vitiligo. Especially preferred active ingredients which can be used in combination with the compounds of the invention are Calcineurin inhibitors, for example Cyclosporin A, Cyclosporin G, Cyclosporin B, Cyclosporin C, Cyclosporin D, Dihydrocyclosporin D, Cyclosporin E, Cyclosporin F, Cyclosporin H, Cyclosporin I, ASM-240, Pimecrolimus, Tacrolimus, 13-Desmethyl-derivatives of Tacrolimus (L-685487), L-683519 and/or 17-Ethyl-derivatives of Tacrolimus, preferably Pimecrolimus, Tacrolimus, or Cyclosporin A, especially preferably Tacrolimus, steroid, for example Betamethasone, Betamethasone-17-valerate, Fluocinolone, Triamcinolone, Triamcinolone acetonide, clobetasol, clobetasol propionate, halobetasol, hydrocortisone, cortisone, desonide, Prednisolone, paramethasone, Methylprednisolone, Dexamethasone, Deflazacort, Vitamin D analogues, especially calcipotriol, Pseudocatalase, or other active ingredients which were suggested for vitiligo treatment like levamisole, Fluorouracil, alpha-MSH, Clofazimine, Thiambutosine BP, Chloroquine, Penicillamine, Tar, Minoxidil, Inosiplex, Mechlorethamine, Cyclophosphamide, Anapsos, Antioxidants like *Gingko biloba,* Canthaxanthine, beta-carotene, alpha-Tocopherol, combination of alpha-Tocopherol, ubiquinone, seleno-methionine and methionine, Pentoxifylline, vitamins and trace elements, like Vitamin B12, folic acid, vitamin C, vitamin E, copper salts, human placental extract, khellin and phenylalanine.

In an especially preferred embodiment, a PDE 5 inhibitor useable according to the invention or an isomer thereof, or a pharmaceutically acceptable salt thereof are combined with a compound selected from the group of Pimecrolimus, Tacrolimus, and Cyclosporin A. Especially preferred are combinations of a PDE5 inhibitor selected from Tadalafil and Sildenafil or a pharmaceutically acceptable salt thereof and a compound selected from the group of Pimecrolimus, Tacrolimus, and Cyclosporin A.

In another embodiment, the invention relates to the use of one of the above-mentioned compositions for the manufacture of a medicament for the treatment and/or prevention of hypopigmentary disorders, especially vitiligo. The same administration forms as discussed above for PDE 5 inhibitors useable according to the invention or an isomer thereof or a pharmaceutically acceptable salt thereof alone, are suitable for the compositions, especially the topical application on lesions for treatment, or on unaffected skin for prevention. In another aspect of the present invention, the active ingredients are administered together or spatially and/or temporally separated.

In another aspect the present invention relates to treatments for hypopigmentary disorders, especially vitiligo comprising administration of a medicament containing PDE 5 inhibitors useable according to the invention or an isomer thereof, or a pharmaceutically acceptable salt thereof alone and administration of one or more further treatment forms which are known to be suitable for the treatment and/or prevention of vitiligo. Preferred treatment forms which can be combined with the treatment with a medicament containing PDE 5 inhibitors useable according to the invention or an isomer thereof, or a pharmaceutically acceptable salt thereof alone, and optionally other active substances, are PUVA treatment, KUVA treatment, heliotherapy, climatotherapy, especially at the Dead Sea, Laser therapy, for example low energy laser therapy, ultrapulse carbondioxide laser therapy, short pulse carbondioxide laser therapy or Ruby laser therapy, surgical therapies like minigraft, suction epidermal grafting, dermo-epidermal grafts, epidermal suspensions, in vivo cultured epidermis and melanocyte suspensions, or UVB treatment.

Assays for Testing Subject Compounds

In general, tests for measuring the effect on hypopigmentary disorders are described in the prior art. For example, an in vitro model consisting of keratinocytes and melanocytes may be used. E.g. the commercially available MelanoDerm Skin Model (MatTek Corporation, Ashland, Mass.) uses NHEK (normal human derived keratinocytes)-NHEM (normal human derived melanocytes) co-cultures (MelanoDerm Skin model) to model the human epidermis taking into account that melanocytes are dependent on keratinocyte signalling. NHEKs are cultivated in culture inserts placed on the NHEM monolayers according to the instructions of the manufacturer (MatTek Corporation, Ashland, Mass.). NHEMs undergo spontaneously melanogenesis up to 3 weeks of culturing. Regarding evaluation of pharmaceutical agents to stimulate skin pigmentation as needed for treating hypopigmentary disorders, the tissues darken faster than untreated controls.

Other in vitro assays for determining the effect of a subject compound on hypopigmentary disorders are in vitro assays based on melanin content analysis.

Melanin content analysis assays are also described in the prior art.

For example, treated and control melanocytes are harvested by trypsinization. Ten percent of the melanocytes are removed and counted on a Coulter counter. The remaining melanocytes are centrifuged and the resulting cell pellet is washed in phosphate-buffered saline pH 7.4 and re-centrifuged. The cell pellet is then dissolved in 1 ml of 1 M sodium hydroxide. The optical density of this solution is measured spectrophotometrically at 405 nm and is compared to synthetic melanin to determine melanin content per cell. A higher melanin content reflects enhanced pigmentation.

Similarly, the assay can be performed as follows: treated and control melanocytes are harvested by trypsinization, washed with phosphate-buffered saline (PBS), suspended in 500 µl PBS, and counted. The cells are then solubilized by adding 500 µl of 10N NaOH and incubating for 30 min at room temperature. Absorbance at 475 nm is measured and compared with a standard curve for synthetic melanin.

Alternatively, the $^{14}$C-tyrosine melanin-formation assay can be used, which measures the radioactive melanin formed when $^{14}$C-tyrosine is converted to the acid-insoluble melanin biopolymer. For this assay, cell extracts from treated and control cells are incubated with $^{14}$C-tyrosine for 1 hour and absorbed on filter paper. The filter paper is dried then washed in 0.1 mol/L hydrochloric acid three times and placed in a scintillation vial with 5 ml scintillator solution. The radioactivity is counted in triplicate using the same scintillator counter.

Alternatively, the effect of a compound on a hypopigmentary disorder can be determined by measuring tyrosinase activity, which are well described in the prior art.

For example, tyrosinase activity of cell culture can be determined: treated and control melanocytes are incubated with 1.0 µCi [$^3$H]tyrosine per ml. 700 µl of 10% trichloroacetic acid containing 20% charcoal (charcoal solution) is added to the medium (700 µl), and the mixture is mixed in a vortex for 30 s and then centrifuged at 10,000 rpm for 10 min. Seven hundred microliters of the supernatant is transferred into a new tube and treated twice with the charcoal solution. The radioactivity of the final supernatant is determined in a liquid scintillation counter.

Alternatively, tyrosinase activity can be determined in cell extracts. For example, treated and control melanocytes are collected and washed twice with PBS, and then lyzed in 0.1 M sodium phosphate buffer (pH 6.8) containing 1% Triton X-100. After determining the protein content in the cell extract, 10 µg of each extract is incubated in 100 µl of 100 mM sodium phosphate buffer (pH 6.8) containing 1.0 µCi [$^3$H] tyrosine per ml, 5 µg L-dihydroxyphenylalanine, and 1% Triton X-100 for 15 min at 37° C. After adding 900 µl of charcoal solution, the samples stand for 20 min at 4° C. and then are centrifuged at 10,000 rpm for 10 min. The supernatants are applied to a 0.2 ml Dowex-50 column equilibrated in 10% trichloroacetic acid and washed with 0.5 ml of 10% trichloroacetic acid, after which the radioactivity of the effluents is determined in the liquid scintillation counter.

Also, some animal models of varying predictability and suitability exist. An evaluation of suitability of various vitiligo animal models is described in Vitiligo (eds. S. Hann and J. J. Nordlund, Blackwell Science, Chapter 33: Animal models by L. Lamoreux and R. E. Boissy)

For example, the Smyth chicken exhibiting a genetically inherited form of vitiligo-like depigmentation resulting from the loss of melanocytes in feathers is discussed as vitiligo model. The pigmentation phenotype of this animal model appears to involve an immune response. Also, the so-called vitiligo mouse is described. In this model no immune component is involved and the disorder is not polyfactorial; i.e. unlike in humans.

Vitiligo, for example, is not a simple, one-locus-disease, and inheritance is not its only cause. Therefore, in the case of vitiligo, animal models must be used with the knowledge that the disorder observed in the genetically defective animal will not be homologous with the disorder of the average human vitiligo patient. Thus, the study of one animal model, especially if the defect is caused by one gene locus in the model, need not be more predictive than an in vitro model.

None of the aforementioned tests has proved particular useful on its own when it came to identifying compounds useful in the treatment and/or prevention of hypopigmentary disorders, given that not many compounds are known to have a pronounced positive effect on the onset of hypopigmentary disorders. This shortcoming of the prior art has now been overcome, in that the present inventors have found that surprisingly PDE 5 inhibitors useable according to the invention or an isomer thereof, or a pharmaceutically acceptable salt thereof, as defined before, provide for compounds which have a beneficial effect on hypopigmentary disorders, especially on vitiligo. Therefore, according to another aspect of the present invention, it provides for the use of PDE 5 inhibitors useable according to the invention or an isomer thereof, or a pharmaceutically acceptable salt thereof, as defined above, in a screening assay for compounds which are suitable for the treatment and/or prevention of hypopigmentary disorders. In one embodiment, such screening assay is an in-vitro-model consisting of a co-culture of keratinocytes and melanocytes as described above. In another embodiment the screening assay is an in-vitro-assay based on melanin content analysis, as described above. In another embodiment, the screening assay is based on the measurement of tyrosinase activity, as described above. In yet another embodiment, the screening assay is based on an animal model, as described above.

In all these screening assays the PDE 5 inhibitors useable according to the invention or an isomer thereof, or a pharmaceutically acceptable salt thereof serve as positive controls in that they inhibit/prevent the onset of hypopigmentary disorders, especially vitiligo and the response of the assay system towards these controls is compared with the response of the assay system towards a subject compound to be tested.

FIG. 1 shows the influence of Sildenafil on dendrite formation in melanocytes in a melanocyte dendrite outgrowth assay described below. Positive control is IBMX i.e. 3-isobutyl-1-methylxanthin, a compound known to increase melanocyte dendricity. The dendricity of untreated melanocytes was set as 1 in each experiment.

EXAMPLES

Example 1

Effect of Sildenafil on Melanocyte Function

A possibility to test the effect of a compound on melanocyte function as a measure for pigmentation, the melanocyte dendrite outgrowth assay can be performed. Vitiligo melanocytes for example have only stubby dendrites. Increasing dendricity as a prerequisite for the transfer of the melanosomes from melanocytes to the surrounding keratinocytes rescues this defect.

For this assay, cells from a human melanoma cell line (Mel-Ho) were obtained from DSMZ (Deutsche Sammlung für Mikroorganismen and Zellkulturen) and were cultured according to the protocol provided by DSMZ. In short, after thawing the melanocytes were cultured in T-75 flasks in melanocyte culture media (provided by the manufacturer) until they reach 70-80% confluency. The melanocytes were then trypsinized, transferred into 5-10 new T-75 flasks, and grown again to same confluency as described above. After this expansion step the melanocytes were immediately used for the Melanocyte Dendrite Outgrowth Assay or were frozen for later use.

For the assay, the melanocytes were seeded in 24 well plates at a density of $1-5 \times 10^4$ cells/well. After 24 hours, the melanocytes were treated with 100 μM IBMX (Sigma-Aldrich) or different concentrations of Sildenafil and Tadalafil for 24 hours. IBMX (=3-isobutyl-1-methylxanthin) is known to cause increased melanocyte dendricity and was used as a positive control. Cells treated with media only were used as a negative control. Melanocyte dendrite outgrowth was documented by digital photography (Canon G2 Powershot) after 3, 6 and 24 hours. In addition, melanocyte dendricity was scored by 3 blinded individuals after 24 hours. The score ranges from 1 to 4; 1 representing melanocytes with no dendrites and 4 representing melanocytes with many long and branched dendrites. The scoring result of 3 individual experiments performed with Sildenafil is shown in FIG. 1. FIG. 1 shows the negative control treated with media only, exhibiting a score of 1, whereas in the positive control, i.e. IBMX-treated cells, the score reached >3. Surprisingly it was found that also Sildenafil-treated cells, dendricity was strongly stimulated (score >3). 10 μM Sildenafil was used to obtain an score of >3, however also lower concentrations (down to 10 nM) of Sildenafil was sufficient to induce dendrite formation.

Example 2

Effect of Tadalafil on Melanocyte Function

The experiment was performed as described in Example 1, however using Tadalafil as active component.

The results obtained for Tadalafil were very similar to the results obtained with Sildenafil.

It was found that also Tadalafil effectively induces dendricity in melanocytes which proves good suitability of the compounds useable according to the invention for treating and/or preventing hypopigmentary disorders, especially vitiligo.

In summary, the strongly increased dendricity induced by Sildenafil and Tadalafil proves good suitability of the compounds useable according to the invention for treating and/or preventing hypopigmentary disorders, especially vitiligo.

Example 3

Effect of PDE5 Inhibitors on Pigmentation In Vitro

In order to test the effect of PDE5 inhibitors on pigmentation, an in vitro model consisting of keratinocytes and melanocytes is used, namely the commercially available MelanoDerm Skin Model (MatTek Corporation, Ashland, Mass.). This model uses NHEK (normal human derived keratinocytes)-NHEM (normal human derived melanocytes) co-cultures (MelanoDerm Skin model) to model the human epidermis taking into account that melanocytes are dependent on keratinocyte signalling. NHEKs are cultivated in culture inserts placed on the NHEM monolayers according to the instructions of the manufacturer (MatTek Corporation, Ashland, Mass.). NHEMs undergo spontaneously melanogenesis up to 3 weeks of culturing. Regarding evaluation of pharmaceutical agents to stimulate skin pigmentation as needed for treating hypopigmentary disorders, the tissues darken faster than untreated controls. It is expected that both Sildenafil and Tadalafil induce pigmentation in that model compared to the negative controls.

The invention claimed is:

1. A method of treating hypopigmentary diseases or disorders comprising
   administering a PDE5 inhibitor to a patient suffering from a hypopigmentary disease or disorder,
   wherein said PDE5 inhibitor is selected from tadalafil or an isomer thereof or a pharmaceutically acceptable salts thereof, and
   wherein said hypopigmentary disease or disorder is vitiligo.

2. The method according to claim 1, further comprising administering said PDE5 inhibitor topically or systemically or via a combination thereof.

3. The method according to claim 2, further comprising administering said PDE5 inhibitor in the form of a medicament that is in the form of an ointment, a gel, a plaster, an emulsion, a lotion, a foam, a cream of a mixed phase or amphiphilic emulsion system, a liposome, a transfersome, a paste or a powder, or a solution or suspension.

4. A method of treating hypopigmentary disorders comprising administering a composition comprising PDE5 inhibitor and one or more further active ingredients suitable for the treatment of hypopigmentary disorders to a patient suffering from a hypopigmentary disorder wherein said PDE5 inhibitor is selected from Tadalafil, or an isomer thereof, or a pharmaceutically acceptable salts thereof, and wherein said hypopigmentary disease or disorder is vitiligo.

* * * * *